United States Patent [19]
Dolan et al.

[11] Patent Number: 5,229,842
[45] Date of Patent: Jul. 20, 1993

[54] METHOD AND APPARATUS FOR CONTROLLING FLUORESCENT LAMP MERCURY VAPOR PRESSURE

[75] Inventors: Bernard J. Dolan, Winchester; Roman C. Daum, Natick, both of Mass.

[73] Assignee: Dolan-Jenner Industries, Inc., Woburn, Mass.

[21] Appl. No.: 685,927

[22] Filed: Apr. 12, 1991

[51] Int. Cl.⁵ .............................................. G01N 21/84
[52] U.S. Cl. ................................. 356/429; 356/316; 355/30; 313/28; 315/111.01; 315/116; 315/117; 315/118
[58] Field of Search ............... 356/429, 311, 316, 317; 355/30, 215, 52–54, 43, 45, 60; 313/28, 15, 39; 315/57, 50, 116, 117, 118, 111

[56] References Cited
U.S. PATENT DOCUMENTS

| | | | |
|---|---|---|---|
| 1,435,192 | 11/1922 | Anderson | 313/28 |
| 4,772,128 | 3/1988 | Vinarub et al. | 356/384 |
| 5,073,796 | 12/1991 | Suzuki et al. | 355/30 |

OTHER PUBLICATIONS

GTE-Sylvania Brochure-Engineering Bulletin-0-341 Fluorescent Lamps.

Primary Examiner—Vincent P. McGraw
Assistant Examiner—LaCharles P. Keesee
Attorney, Agent, or Firm—Hamilton, Brook, Smith & Reynolds

[57] ABSTRACT

A fluorescent lamp light output is maximized by cooling the cathode regions. Mercury vapor pressure is maintained at an optimum or desired level for light production by cooling the cathode areas of the lamp. The cooled cathode areas of the lamp collect cathode emissive material and mercury vapor condensates. Thus, the light output remains uniform and constant. The functional length of the lamp is not degraded by the deposition of either cathode material or mercury vapor condensates. Cooling can be effected by forcing cool air against the exterior of the lamp adjacent the cathodes or by using forced water heat exchangers. By cooling the respective cathode regions equally, the amount of deposition in the respective regions is substantially the same. Thus, gradations of deposition are avoided. The constant high output fluorescent lamp can be used with electronic inspection equipment and machine vision measurement devices. The inspection equipment and machine vision devices can detect signals with a single photodetector or an array of photodetectors. Optical fiber receivers and transmitters can be used to deliver a reflected light signal or image to associated electronic processing equipment.

26 Claims, 6 Drawing Sheets

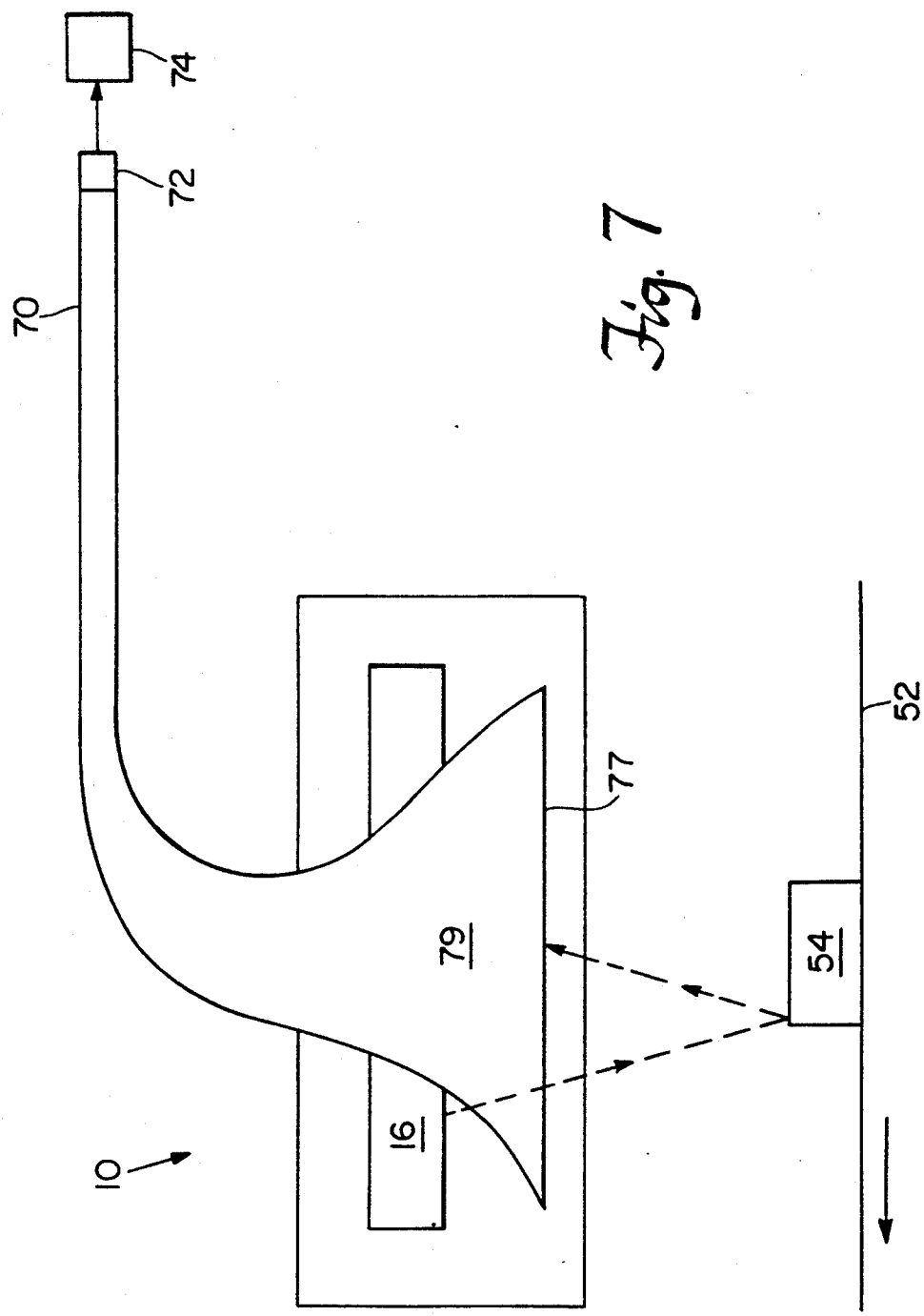

METHOD AND APPARATUS FOR CONTROLLING FLUORESCENT LAMP MERCURY VAPOR PRESSURE

BACKGROUND OF THE INVENTION

Fluorescent lamps have been in common usage for many years. Such lamps are typically used in commercial or residential lighting. However, they are also used in industrial lighting circumstances. For example, fluorescent lamps can be used as an illumination source in electronic inspection equipment and machine vision measurement devices. Precise electronic inspection equipment requires high amplitude, invariant light sources. A common problem with standard fluorescent lamps is the variation in light output and uniformity. In high temperature environments, the internal vapor pressure of fluorescent lamps will increase and as a result the efficiency of the lamps drops dramatically. Losses as high as 40% have been detected in high temperature environments. Moreover, material emitted from the cathodes deposit along the length of the tubes of the lamp. As a result, the lamp light output uniformity decreases where the deposits darken the interior of the tubes.

SUMMARY OF THE INVENTION

The invention is drawn to a high output invariant fluorescent light source. The invention is directed to a fluorescent lamp apparatus comprising a lamp holder, for holding the fluorescent lamp source and an external cooler for cooling only exterior portions of the lamp proximate to the first and second cathodes to a temperature substantially below temperatures between the cathodes. This cooling of the lamp lowers the mercury vapor pressure in the interior of the lamp and maximizes the lamp light output by maintaining the vapor pressure at an optimum or desired value. The temperature of the ends of the lamp behind each cathode can be controlled to vary the lamp light output. Also, by cooling the lamp cathode areas, excess mercury from the vapor condensates and cathode emissive material condense in these cooler areas only. Thus, the functional length of the lamp is not darkened by deposits and the light output remains constant over the life of the lamp. By restricting deposition of the emissive materials and condensates to the respective cathode areas, darkening is avoided along the length of the lamp.

Cooling can be achieved by several methods. In the preferred embodiment, forced air is blown against the exterior of the fluorescent lamp in the vicinity of the respective cathodes. A low pressure source of cool air is directed along a first air pipe to the middle of the enclosure. A bifurcated coupling attached to the first air pipe directs the forced air from the middle of the enclosure along a second pipe and a third pipe where the air exits in the vicinity of the respective cathodes of the bottom of the lamp between the cathode and the end of the lamp. Thus, low pressure air supplies, which are commonly found in most factories, can be easily accessed to provide cooling with or without a controlled cooling chamber for the lighting source. Moreover, where precise control of the lamp pressure and thus the light output is required, a temperature regulated air source can be used. A plurality of air outlet apertures are placed along the enclosure exterior to control enclosure pressurization and the maximum enclosure temperature which is ambient to the lamp.

Other methods of cooling can also be used. For example, a forced water system in conjunction with heat exchangers positioned near the respective cathodes of the lamp can be used to provide cooling at the respective cathodes. The water temperature can also be regulated to provide more accurate control of the lamp vapor pressure and lamp output.

This method of controlling a fluorescent lamp output is not limited by the shape of the lamp or the composition of the vapor material. It is applicable to all lamps with a plurality of cathodes which suffer from varying uncontrolled light output due to darkening from deposits of cathode emissive material as well as excessive lamp mercury vapor pressure. This method and apparatus can be applied to regular fluorescent lamps, high output fluorescent lamps and very high output fluorescent lamps. Thus, it can be advantageously used in conjunction with an electronic inspection device. For example, the invention is also drawn to an inspection system comprising a high output and invariant fluorescent light source including an enclosure, a mercury vapor fluorescent lamp which emits radiation at a first wavelength including a first cathode and a second cathode. A lamp holder attached to the interior of the enclosure for holding the fluorescent lamp within the enclosure and electrically connecting the first and second cathode to a power source to activate the lamp. An external cooler for directing a cooling fluid in a heat exchange relationship with the ends of the lamp, behind each cathode to control the mercury vapor pressure of the lamp and maximize or control the light output produced wherein cathode emissive material and mercury condensates are only deposited at the cool cathode regions and the functional length of the lamp is free of deposits. A moving web with a target material which reflects light from the lamp and emits radiation at a second wavelength in response to lamp light at the first wavelength is illuminated by the lamp. An optical fiber image collector and optical fibers coupled to the light source collect and guide the light reflected and emitted by the target. A photodetector, or an array of photodetectors, or charge coupled devices (CCD) can be located at a specific location or along the entire length of the fluorescent lamp. The photodetectors are coupled to the optical fiber or optionally coupled to a coherent image or noncoherent optical fibers which act as a receiving aperture to remotely transmit reflected light energy and/or an image to the photodetectors. A single detector or a string of a plurality of detectors can be located adjacent to the lamp tube or adjacent to a rectangular aperture of the optical fiber or remotely located at the end of the lamp or remotely located near a separate image processing device. Thus, highly reliable and consistent readings can be obtained from such an inspection system using the high output and invariant fluorescent source of the invention. The cooling system allows the fluorescent lamp to operate at its maximum uniform output which is invariant to lamp surface temperatures over the life of the lamp. As a result, fewer lamps are needed for a given application. Thus, less wiring and circuitry are required. Lower maintenance costs are involved by using the light source of the invention.

In the inspection system, the cool temperature, stable regions of the lamp provide a convenient location for the detectors. Thus, the proximity of the light source and photodetector to the target provide an optimum signal to noise ratio. Alternatively, the photodetector can be positioned remotely from the light source or within the enclosure or further remoted to an electronic interface.

A filter can be imposed between the target and the photodetector for blocking radiation at the first wavelength emitted by the light source and passing light at the second wavelength emitted by the target. Thus, the photodetector can be isolated from the light of the lamp source.

The above and other features of the invention including various novel details and construction and combination of parts will now be particularly described with reference to the accompanying drawings and pointed out in the claims. It will be understood that particular device embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 7 shows a schematic illustration of an inspection system using the cooled fluorescent light source of the invention with remote detectors.

DETAILED DESCRIPTION OF THE INVENTION

Figure 1:
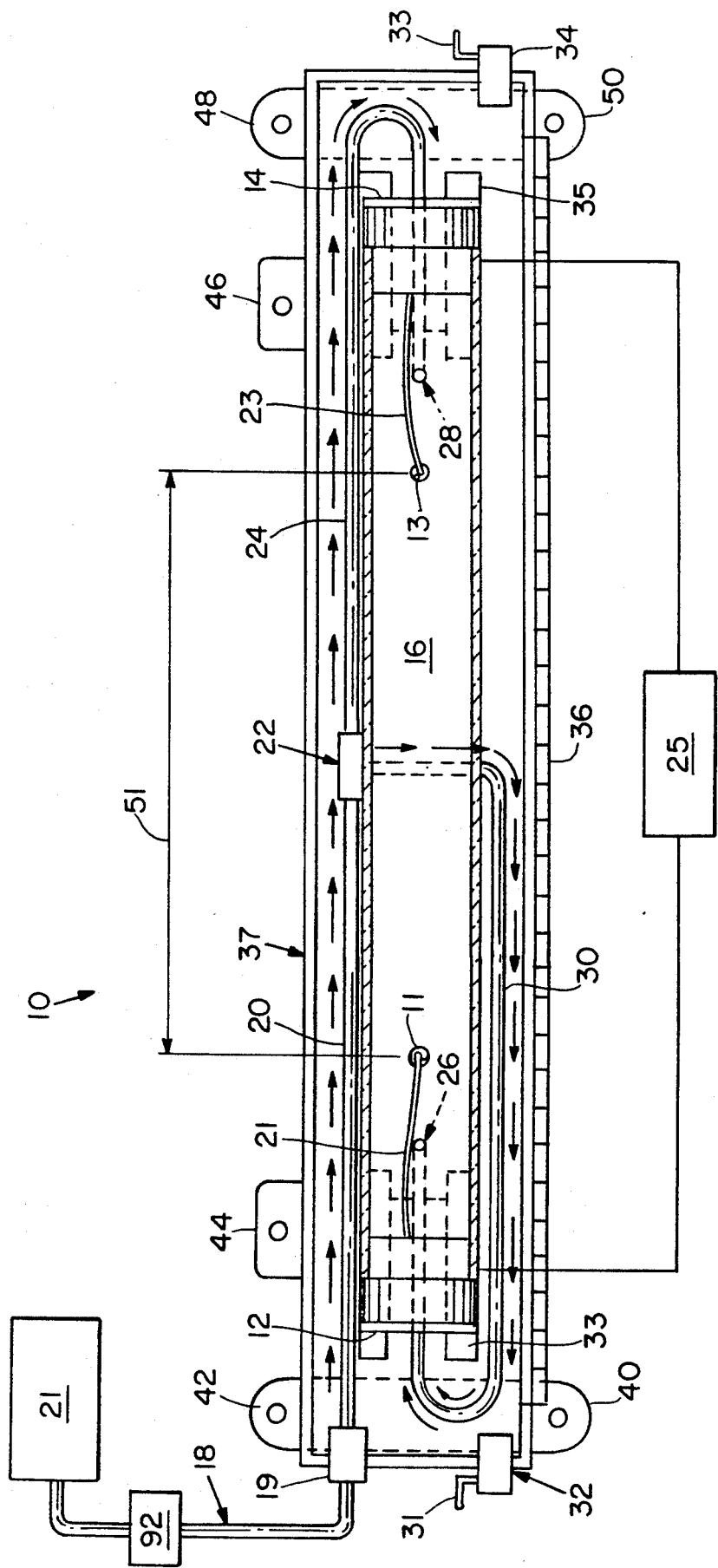
FIG. 1 illustrates a top view of a fluorescent lamp enclosure cooled by forced air.
Figure 2:
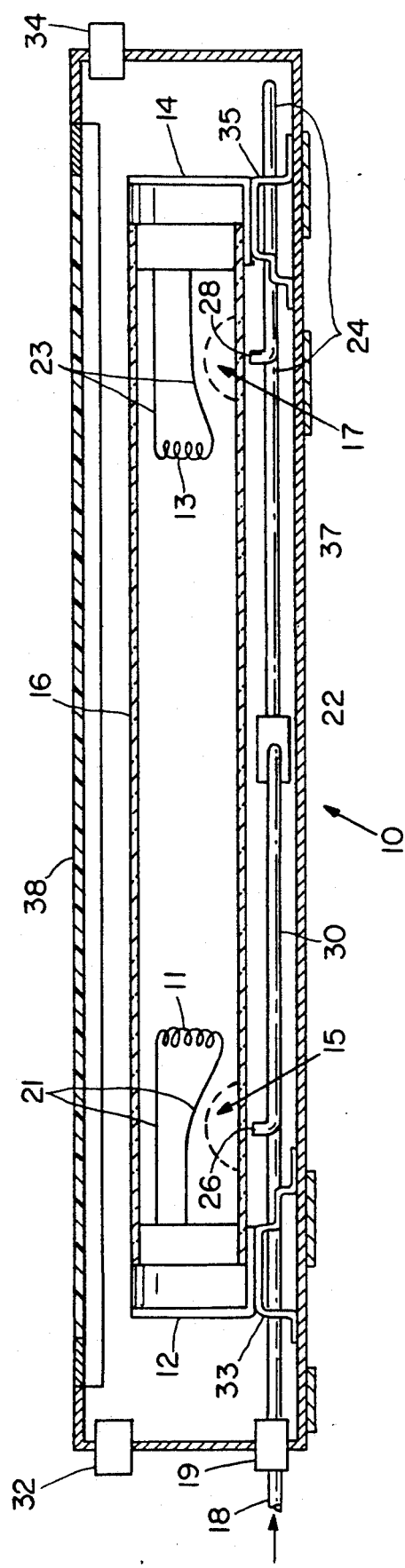
FIG. 2 illustrates a side view of the invention of FIG. 1.

FIGS. 1 and 2 illustrate the preferred embodiment of the invention for maximizing fluorescent light output and maintaining that maximized output constant over the life of the lamp. Fluorescent lamp 6 is held in enclosure 10 by lamp holders 12 and 14. Lamp 16 can be a regular fluorescent lamp or a high output (HO) fluorescent lamp or a very high output (VHO) fluorescent lamp. The functional length 51 of the lamp denotes the region of effective illumination. These lamps use the electric discharge to generate internal ultraviolet radiation by exciting mercury vapor. That radiation activates a coating of fluorescent material such as phosphorous on the inner surface of the glass tube of the lamp. Thus, the invisible ultraviolet radiation is converted into visible light. Electrical activation of the mercury vapor is effected by means of cathodes 11 and 13 as shown in FIGS. 1 and 2. Lamp holders 12 and 14, in conjunction with leads 21 and 23, provide the electrical connection to power source 25 which drives the lamp. Lamp holder struts 33 and 35 couple the lamp holders to the wall 37 of enclosure 10.

Figure 4:
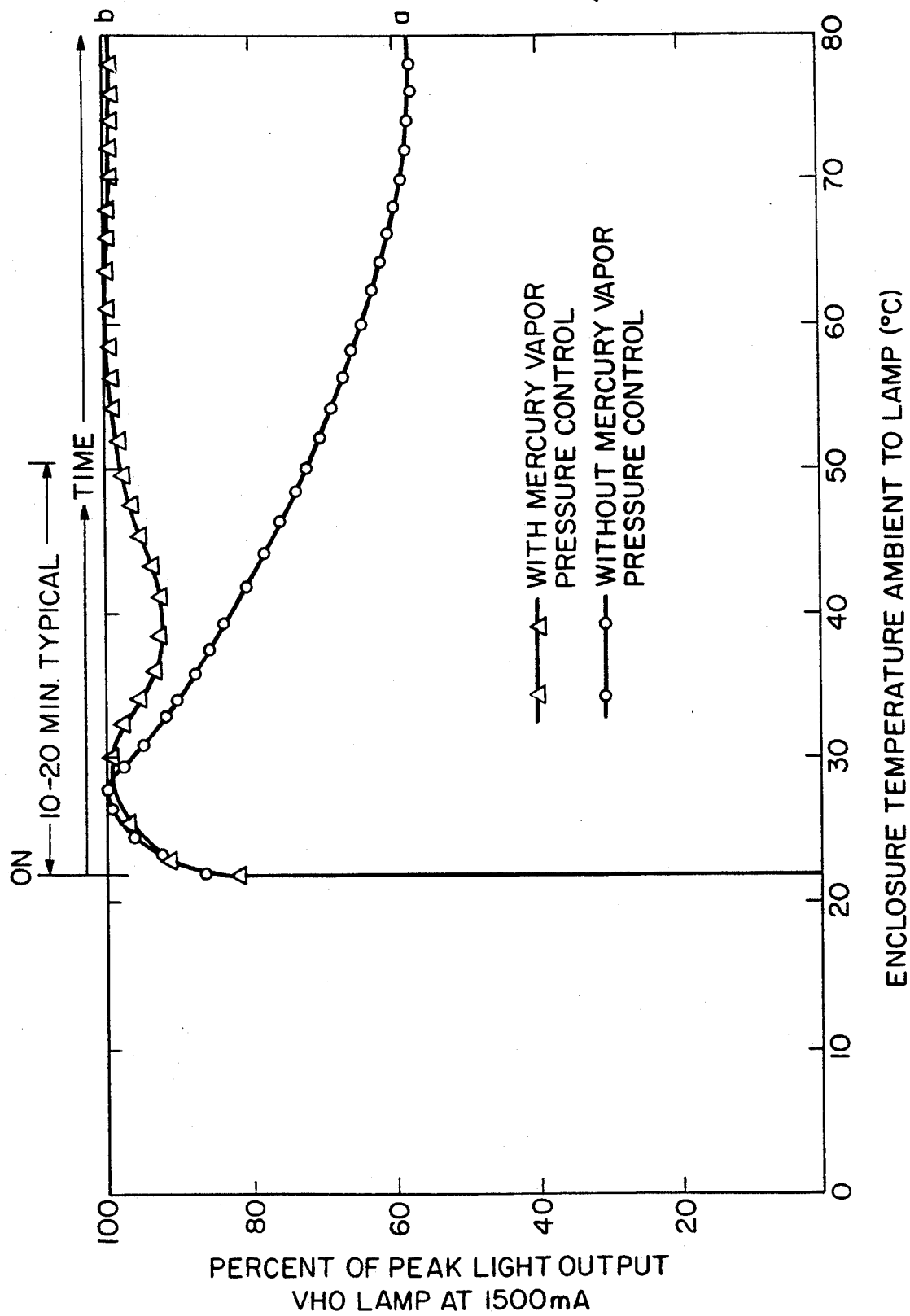
FIG. 4 illustrates the effective light production of the cooled light source with mercury vapor pressure control of the invention versus a device without a cooling feature or mercury vapor pressure control.

FIG. 4 illustrates the light output response of a lamp which is cooled in accordance with the invention and the light output response of a standard receptacle without mercury vapor pressure control. Typically, fluorescent lamps are held in an enclosure. For a standard lamp, as the enclosure temperature ambient to the lamp approaches 30° C., the light output peaks and drops dramatically as the ambient temperature increases and the mercury vapor pressure increases. Light output drops by as much as 40%. See graph a. However, by cooling the region of the lamp close to the cathodes, the mercury vapor pressure can be controlled to remain at an optimum or desired level regardless of the ambient temperature of the enclosure. See graph b. Moreover, as will be shown, this maximum output is invariant with time because depositions of cathode material and mercury vapor condensates occur only in the cool regions behind the cathodes. Thus, the functional central length 51 of the lamp output is uniform and unaffected by the deposits. As shown in graph b of FIG. 4, the light amplitude can be varied by selecting the cooling temperature. For example, if the lamp ends were cooled to 40° C., the light amplitude would be lessened by approximately 10%. Thus, light dimming can be achieved without using expensive and sophisticated electronic control circuits.

In the preferred embodiment, this result is achieved by blowing cool air at a selected temperature, typically between 20°-35° C., onto the exterior of the fluorescent lamp in the vicinity of the first and second cathodes at the bottom of the lamp, to achieve the desired output. FIG. 2 illustrates cooled regions 15 and 17. These cooled areas represent the coldest spot on the lamp. Thus, the coolest areas, 15 and 17, serve as control centers for mercury vapor pressure. The cooling controls the mercury vapor pressure and sets that pressure at an optimum or desired level throughout the lamp to produce a maximized or controlled light output. This light output remains constant and uniform because the interior of the lamp along its functional length 51 does not receive any cathode emissive material deposits or mercury condensates. The emissive material and mercury are most likely to deposit or condense out at lower temperatures and tend to stay entrained in the gas in hotter regions that exceed ambient enclosure temperatures. The materials are thus removed from the gaseous environment in the cool regions. The coolest areas, 15 and 17, collect all deposit materials and thus prevent any from being deposited on the functional length 51 of the lamp. The respective ends of the lamp associated with the respective cathodes are cooled equally to assure equal deposition at the ends of the lamp only.

Most factories have sources of low pressure air in the range of 5 to 20 psi. Thus, the enclosure of the invention can be easily attached to a source of cool air. Element 81 in FIG. 1 represents such a factory source of cool air, with an optional controlled cooling chamber 92. Air from low pressure source 21 is driven through air pipe 18 through the input aperture 19 to air pipe 20. The distal end of air pipe 20 terminates in a bifurcated coupling 22, located at the enclosure center. Dividing the air at the middle of the enclosure, assures that both air streams travelling through air pipe 24 and air pipe 30 within the enclosure heated by the lamp will be at the same temperatures. The distal end of air pipe 30 terminates in aperture 26 proximate to the first cathode 11 and blows cool air against the lamp at cooling area 15. The distal end of air pipe 24 terminates in air output aperture 28 proximate to the second cathode 13 and blows cool air against the bottom of the lamp at cooling area 17. The air pipes can be comprised of nylon or other high temperature resistant plastic. Apertures 26 and 28 have a diameter of 0.04 inches and are positioned 1/5 to ¼ of an inch from the lamp envelope and midway to ¼ of a distance between the lamp cathode filament plane and the end of the lamp.

By effectively cooling the ends of the lamp and restricting deposits to those ends, the functional length of the lamp remains constant. Thus, a constant uniform light source is produced of a desired high amplitude which could be used to detect the quantity or quality of defects in a web. For example, the amount and degree of holes and tears in a web of paper can be determined. For such an inspection system, optimum and uniform lighting of the target is a prerequisite. However, such lamps typically produce tremendous amounts of heat. Thus, the cooling device of the invention represents a simple and effective method of achieving high light amplitudes which are invariant regardless of the ambient temperature. By cooling the lamp, the mercury vapor pressure is controlled so that the lamp operates most efficiently.

Although the preferred use is in electronic inspection or machine vision applications this cooling technique is applicable to all fluorescent lamps. For example, it can be used with residential fluorescent illumination or decorative lamps. The invention can be used to cool straight or curved lamps. Although the preferred embodiment is a closed enclosure, the cooling technique of the invention can be applied to open enclosures. The maximum enclosure temperature, ambient to the lamp, and the enclosure pressurization is controlled by varying the size of air outlet apertures 32 and 34. Stopcocks 31 and 33 control the flow of air through air outlet apertures 32 and 34. By pressurizing the enclosure, interior air currents are prevented. Without pressurization, air would leak throughout the enclosure and generate cool areas at other than the lamp ends. Thus, deposits would collect on the functional length of the lamp.

Figure 3:
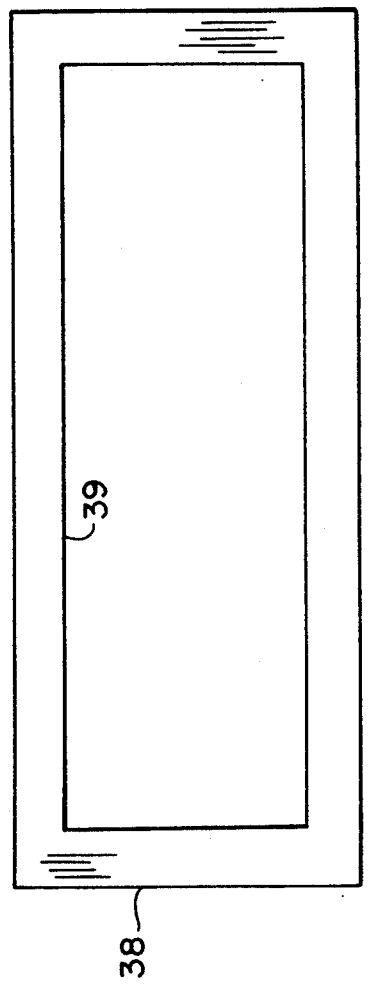
FIG. 3 illustrates a cover with an aperture for the enclosure of the invention of FIG. 1.

The outer wall 37 of the enclosure conforms to National Electrical Manufacturers Association (NEMA) standards and can be water splash proof and air tight. The enclosure can be fixed by means of brackets 40, 42, 44, 46, 48 and 50. Hinge 36 permits cover 38 to pivot and allow access to the interior of the enclosure. Cover 38 (FIG. 3) includes an aperture 39 through which light from the fluorescent lamp exits. The size and shape of the aperture 39 can be varied to accommodate various illumination requirements.

The cooled enclosure of the invention can be used as a light source in an explosive atmosphere by sealing the enclosure. Air pipes can be attached to the outlet apertures to prevent access to the enclosure interior. For example, the sealed light of the invention can be used in an explosive or a flammable environment. The cooler of the invention permits the enclosure to be sealed and operated efficiently despite high levels of ambient heat. Its high efficiency and consistency of output reduces the number of lamps required for a given application. Thus, it represents a cheaper, low maintenance solution to many lighting problems.

Figure 5:
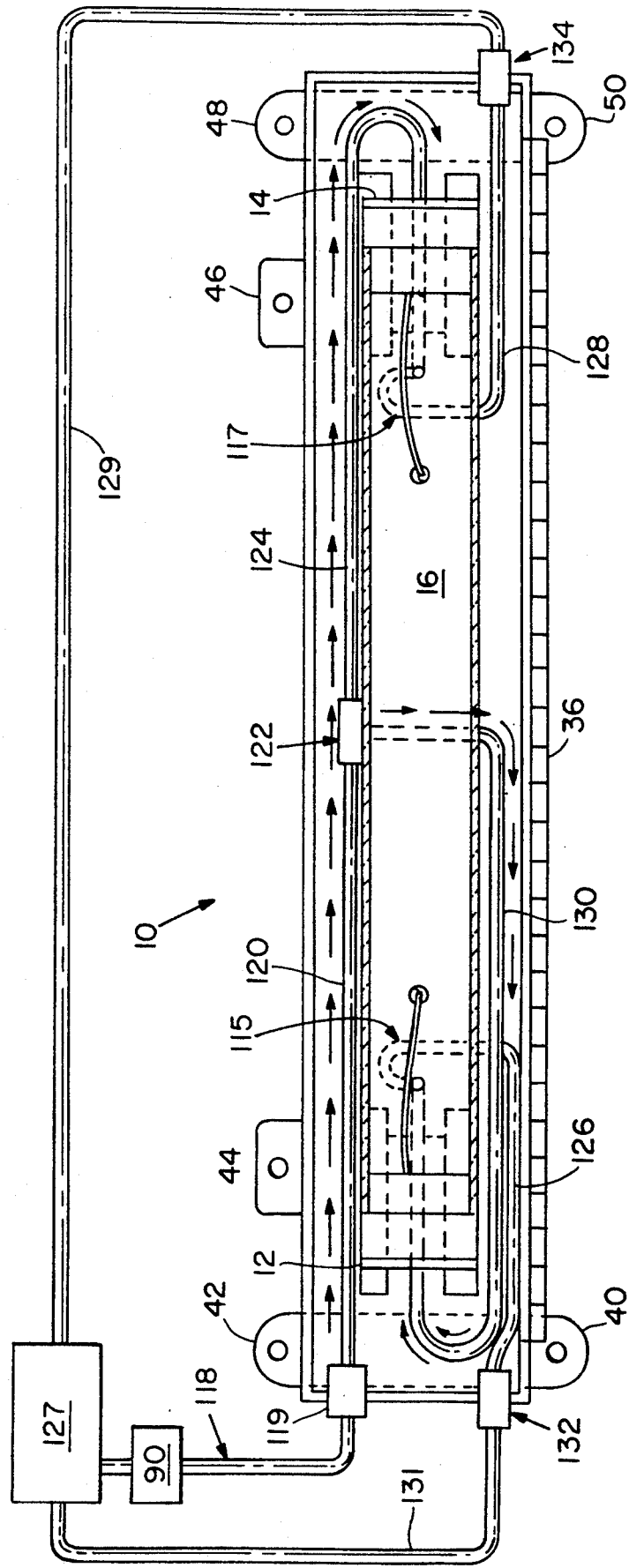
FIG. 5 illustrates a top view of a second embodiment of the invention which uses forced water to cool the lamp.

FIG. 5 illustrates a second embodiment of the invention. In FIG. 5, cooling is effected by means of a forced water supply. Water source 127, including an optional controlled cooling chamber 90, supplies water to pipe 118 and input aperture 119 to water pipe 120. Pipe 120 is coupled to bifurcation 122 and sends equal temperature water streams to the regions of the respective cathodes by means of pipes 130 and 124. Respective heat exchangers 115 and 117 cool respective cathode areas. The heated water is returned to the water source by means of pipes 126, 132, 131, 128, 134 and 129. Again, the cathode regions are cooled equally so that the optimum mercury vapor pressure level is reached and maximum uniform light output is achieved. Also, condensates and emissive materials are deposited only in the cooled areas around the cathodes. Thus, the functional length of the lamp is free of deposits and the amplitude of the light remains unchanged over the life of the lamp.

Greater control of vapor pressure can be achieved by regulating the temperature of either the water or air used to cool the cathode regions of the lamp. Thus, where precise light outputs are required, temperature regulated coolants can be used to optimize the mercury vapor pressure.

Figure 6:
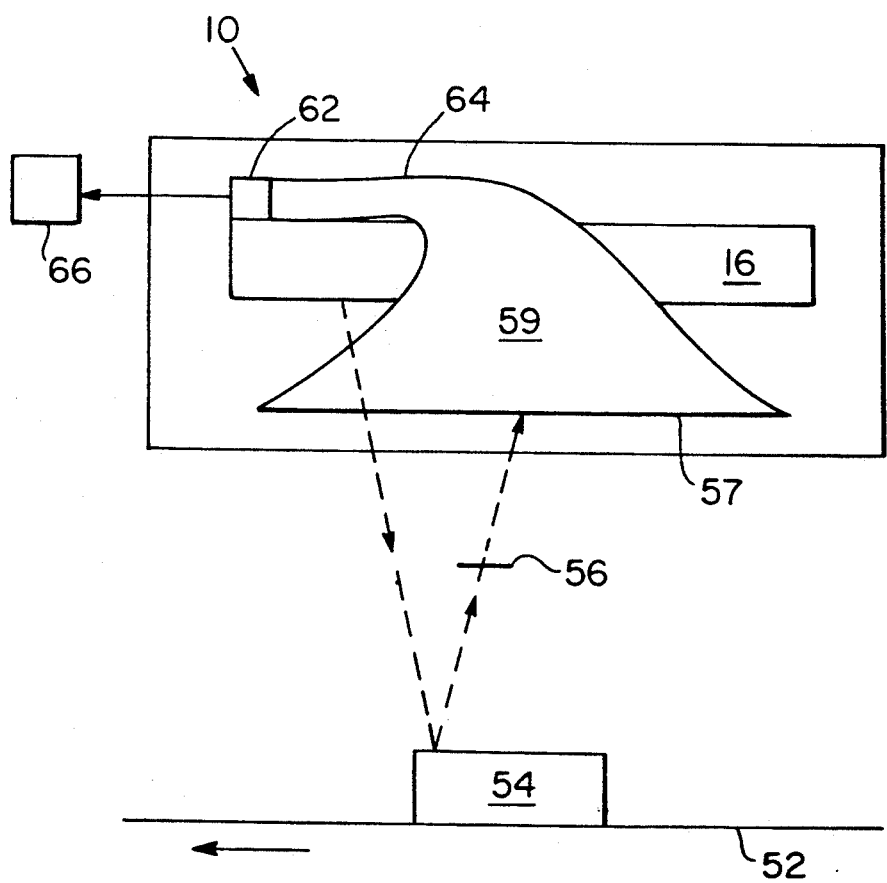
FIG. 6 represents a schematic illustration of an inspection system with an integral light source and detector using the cooled light source of the invention.

FIG. 6 illustrates one inspection application with detectors integral with the light source. Fluorescent lamp 16 is held in an enclosure 10, such as that shown FIGS. 1, 2 and 5, wherein the cathode regions of the lamp are cooled to optimize the mercury vapor pressure and the light output. The cooled areas of the lamp represent thermally stable regions for placement of photodetectors. For example, photodetector 62 is located proximate to a cooling area of the fluorescent lamp. If the photodetector is vulnerable to heat, the cooling fluid of the cooler can be directed at the location of the photodetector, as well as behind the cathode regions of the lamp. Light emitted from the lamp reflects from web 52 and the target 54. Light from target 54 is captured and guided by fiber optic image and/or light collector 59 to photodetector 62. Fiber optic image collector 59 provides isolation from electromagnetic interference (EMI) generated by the fluorescent lamp. The detector transmits the signal to processing circuit 66, which can be image processing devices.

The fiber optic image collector 59 can be a plurality of noncoherent optical fibers. The light capturing surface 57 of the fiber optic image collector 59 is fan shaped. End 64 of collector 59 is coupled to the detector 62. Detector 6 transmits signals to processing circuit 66. Thus, defects on web 52 and target 54 are detected.

The fiber optic image collector 59 can be divided into a plurality of channels. Thus, light capturing surface 57 is delineated into a plurality of segments or channels. The optical fibers from each channel are coupled to a separate detector. In this fashion, noncoherent optical fibers can be used to locate the position of a defect.

Fiber optic image collector 59 can also be a collection of coherent optical fibers for transmitting images. For example, such coherent optical fibers are shown in U.S. Pat. No. 4,772,128, issued to Vinarub et al., which is incorporated by reference herein.

The light detector comprises a single photodetector, or an array of photodetectors or a charge coupled device(s) (CCD) located at a specific location or along the entire length of the lamp. The photodetectors are coupled to the optical fiber collector 59 which, as noted above, can be a coherent image or noncoherent optical fibers which act as a receiving aperture to remotely transmit reflected light energy and/or an image to the photodetectors. A single detector or a string of plural detectors can be located adjacent the lamp tube or adjacent a rectangular aperture of the optical fiber.

As noted previously, target 54 can emit light at a second wavelength in response to light from the lamp at the first wavelength. Filter 56 can be placed in the path of emitted light from target 54 to block light of the first wavelength from the lamp and only transmit light of the second wavelength emitted by the target. Thus, light from the lamp is isolated from the detector and spurious signals avoided. The inspection system of FIG. 6 optimizes the signal-to-noise ratio due to the proximity of the light source and photodetector to the target. Also with a spectrally selected lamp at a desired emittance frequency, the signal-to-noise ratio can be further optimized by use of a filter which blocks the light source wavelength and transmits only the emitted light from the target. Thus, automatic acceptance or rejection of a desired target of a given wavelength is possible.

FIG. 7 illustrates an inspection system where the detectors are located remotely from the light source. Remote fiber optic image collector 79 extends from the enclosure and directs light to remote detector 74. Moreover, the fiber optic image and/or light collector 79 provides isolation from fluorescent lamp EMI. This physically removes the detectors from the noisy electromagnetic atmosphere of the fluorescent lamp source. As noted in the discussion of FIG. 6, the collector 79 can be comprised of coherent or noncoherent fibers. Moreover, the noncoherent fibers can be delineated into channels to denote the position of a defect detected on web 52 or target 54. A capturing surface 77 of collector 79 collects light from the web and target and guides it along remote end 70 to detector 72. A signal processing circuit 74 coupled to detector 72 receives defect information.

The inspection systems of FIGS. 6 and 7 can be used with a machine vision system which is a software based system with an algorithm to measure objects in one, two or three dimensions or an electronic inspection system that requires light reflection or occlusion by a target within a field of view to merely indicate the incidence of defects or the presence of a target which it does not necessarily quantify. The inspection devices could also be used in a transmissive as well as a reflective environment.

The cooling lamps of FIGS. 1, 2 and 5 are not limited to air or water cooling but are applicable to all types of coolants. For example, freon could be used as a coolant. Also, electronic cooling devices such as Peltier devices can be used.

Another advantage to using fluorescent lamps for illumination is the long lamp life. The lifetime of fiber optic quartz halogen lamps typically is only 1000 hours. However, the lifetime of a fluorescent lamp is typically 10,000 hours, and could last as long as 25,000 hours. Also, the need for expensive electronic controllers to regulate the power supply and maintain a constant output for the fluorescent lamp is eliminated by restricting deposits to the ends of the tube by using the invention. Thus, the length of the area of illumination and its amplitude remains constant at a desired level. This is controlled by the degree of cooling. Savings are achieved because of the minimum number of lamps required. Also, maintenance is minimized because of the consistency of the lamp of the claimed invention. Those skilled in the art will recognize, or be able to ascertain, using no more than routine experimentation, many equivalents to the specific embodiments of the invention described herein. These and all other equivalents are intended to be encompassed by the following claims.

I claim:

1. A fluorescent lamp apparatus for a fluorescent lamp with a first cathode and a second cathode, comprising:
   a fluorescent lamp;
   a lamp holder for holding said fluorescent lamp; and
   an external cooler for providing cooling to the fluorescent lamp to lower the vapor pressure in the lamp and thus improve lamp output, said cooling being localized such that substantially all of said cooling is applied to portions of the lamp which are proximate to the first cathode and the second cathode, the temperatures of said portions being lowered to temperatures substantially below temperatures between the cathodes.

2. A fluorescent lamp enclosure for a fluorescent lamp with a first cathode near a first end of the fluorescent lamp and a second cathode near a second end of the fluorescent lamp, comprising:
   a fluorescent lamp having an illumination region between the first and second cathodes;
   a lamp holder for holding said fluorescent lamp; and
   a cooler for directing a cooling fluid in a localized heat exchange relationship with the ends of the lamp, said cooling fluid being directed toward localized portions of the lamp behind each cathode to control the lamp mercury vapor pressure, wherein the cooling of the lamp cathode areas substantially prevents the deposition of cathode emissive material on the illumination region of the lamp.

3. A fluorescent lamp enclosure, as recited in claim 2, wherein the temperature of the ends of the lamp behind each cathode is controlled to maximize the lamp light output.

4. A fluorescent lamp enclosure, as recited in claim 2, wherein the temperature of the ends of the lamp behind each cathode is controlled to vary the lamp light output.

5. A fluorescent lamp enclosure, as recited in claim 2, wherein the cooler further comprises:
   a low pressure source of cool air,
   a first air pipe connected to said cool air source,
   a bifurcated coupling, located in the middle of the enclosure and attached to said first air pipe,
   a second air pipe with a proximal end and a distal end, said second pipe proximal end connected to said bifurcated coupling, said second distal end positioned proximate the first cathode region to expel cool air at the first cathode region at the bottom of the lamp, and
   a third air pipe with a proximal end and a distal end, said third air pipe proximal end connected to said bifurcated coupling, said third air pipe distal end positioned proximate the second cathode region to expel cool air at the second cathode region at the bottom of the lamp.

6. A fluorescent lamp enclosure, as recited in claim 5, wherein the source of cool air is temperature regulated for cooling the air to accurately control the lamp mercury vapor pressure.

7. A fluorescent lamp enclosure, as recited in claim 5, further comprising:
   a plurality of air outlet apertures to control the enclosure pressurization and the maximum enclosure temperature, ambient to the lamp.

8. A fluorescent lamp enclosure, as recited in claim 2, wherein the cooler further comprises:
   a source of cool water, a first water pipe connected to said cool water source, a bifurcated coupling, located in the middle of the enclosure and attached to said first water pipe, a second water pipe with a proximal end and a distal end, said second water pipe proximal end connected to said bifurcated coupling, said second water pipe distal end positioned proximate the first cathode region to cool the first cathode region of the lamp, and a third water pipe with a proximal end and a distal end, said third pipe proximal end connected to said bifurcated coupling, said third water pipe distal end positioned proximate the second cathode region to cool the second cathode region of the lamp.

9. A fluorescent lamp enclosure, as recited in claim 8, further comprising:

a fourth water pipe coupling the second water pipe distal end to the water source, and a fifth water pipe coupling the third water pipe distal end to the water source.

10. A fluorescent lamp enclosure, as recited in claim 8, wherein the source of cool water is temperature regulated for cooling the water to accurately control the lamp mercury vapor pressure.

11. A method for controlling fluorescent lamp mercury vapor pressure comprising the steps of:

(a) holding a fluorescent lamp having a first cathode and a second cathode, and (b) locally cooling localized portions of the fluorescent lamp, to desired control temperatures substantially below temperatures between the cathodes to lower the vapor pressure in the lamp and thus improve lamp output, said localized portions of the fluorescent lamp being proximate to the first cathode and the second cathodes.

12. A method, as recited in claim 11, wherein the step of locally cooling further comprises forcing cool air against the exterior of the fluorescent lamp only in the localized portions of the lamp.

13. A method, as recited in claim 12, wherein the air is temperature regulated to accurately control the lamp vapor pressure.

14. A method, as recited in claim 12, wherein the lamp is held in an enclosure having a plurality of air outlet apertures to control the enclosure pressurization and the maximum enclosure temperature ambient to the lamp.

15. A method, as recited in claim 11, wherein the step of locally cooling is performed by a forced water heat exchanger.

16. A method, as recited in claim 15, wherein the water is temperature regulated.

17. A fluorescent lamp enclosure comprising:

a mercury vapor fluorescent lamp including a first cathode and a second cathode, a lamp holder for holding said fluorescent lamp within the enclosure, and a cooler for cooling localized exterior portions of the fluorescent lamp adjacent the first cathode and the second cathode so that localized lamp regions which are proximate the cathodes are cooled to a temperature which is less than the temperature of an illumination region of the lamp to control the mercury vapor pressure of the lamp, wherein substantial cathode emissive material and mercury vapor condensates are only deposited at the cool cathode regions and the illumination region of the lamp is substantially free of deposits.

18. A fluorescent lamp enclosure, as recited in claim 17, wherein the temperature of the cathode regions of the lamp is controlled to maximize the lamp light output.

19. A fluorescent lamp enclosure, as recited in claim 17, wherein the temperature of the cathode regions of the lamp is controlled to vary the lamp light output.

20. A fluorescent lamp enclosure, as recited in claim 17, wherein the cooler further comprises a supply of low pressure forced air which is directed against the cathode regions of the lamp.

21. A fluorescent lamp enclosure, as recited in claim 17, wherein the cooler further comprises a forced water system including heat exchangers located at the cathode regions of the lamp.

22. An inspection system comprising:

a high output, invariant fluorescent light source including:

an enclosure, a mercury vapor fluorescent lamp which emits radiation at a first wavelength, including a first cathode and a second cathode and an illumination region between the cathodes, a lamp holder attached to the interior of the enclosure for holding said fluorescent lamp within the enclosure, and a cooler for directing a cooling fluid in a localized heat exchange relationship with the ends of the fluorescent lamp, said cooling fluid being directed toward localized portions of the lamp behind each cathode to control the mercury vapor pressure of the lamp and maximize the light output produced, wherein substantial cathode emissive material and mercury vapor condensates are only deposited at the cool cathode regions, and the illumination region of the lamp is substantially free of deposits;

a moving web with a target material which reflects light from the lamp;

an optical fiber image collector and optical fibers coupled to the light source for collecting and guiding light reflected and emitted by the target; and a photo detector, coupled to the optical fibers, for detecting light reflected and emitted by the target.

23. A system, as recited in claim 22, wherein photodetector is positioned proximate the cooled, temperature stable regions of the lamp, to provide an optimum signal to noise ratio due to the proximity of the light source and photodetector to the target.

24. A system, as recited in claim 22, wherein photodetector is positioned remotely from the light source within the light enclosure.

25. A system as, recited in claim 22, further comprising a filter between the target and photodetector for blocking radiation at said first wavelength and passing light at a second wavelength, wherein the target emits radiation at said second wavelength in response to lamp light at said first wavelength.

26. A system, as recited in claim 22, wherein the photodetector is remotely located outside of the enclosure and further comprising an image processing device coupled to said photodetector.

* * * * *